United States Patent
Huang et al.

(10) Patent No.: US 10,618,904 B2
(45) Date of Patent: Apr. 14, 2020

(54) HYDROBROMIDE OF BENZODIAZEPINE DERIVATIVE, PREPARATION METHOD AND USE THEREOF

(71) Applicant: CHENGDU BRILLIANT PHARMACEUTICAL CO., LTD., Chengdu, Sichuan (CN)

(72) Inventors: Haoxi Huang, Sichuan (CN); Guoqing Zhuo, Sichuan (CN); Guoning Shang, Sichuan (CN); Zhen Liang, Sichuan (CN); Ting Chu, Sichuan (CN); Cuicui Chen, Sichuan (CN); Ming Luo, Sichuan (CN); Yingfu Li, Sichuan (CN); Zhonghai Su, Sichuan (CN)

(73) Assignee: CHENGDU BRILLIANT PHARMACEUTICAL CO., LTD., Chengdu, Sichuan (CN)

( * ) Notice: Subject to any disclaimer, the term of this patent is extended or adjusted under 35 U.S.C. 154(b) by 0 days.

(21) Appl. No.: 16/467,866

(22) PCT Filed: Dec. 13, 2016

(86) PCT No.: PCT/CN2016/109564
§ 371 (c)(1),
(2) Date: Jun. 7, 2019

(87) PCT Pub. No.: WO2018/103119
PCT Pub. Date: Jun. 14, 2018

(65) Prior Publication Data
US 2019/0308981 A1    Oct. 10, 2019

(30) Foreign Application Priority Data
Dec. 9, 2016 (CN) .......................... 2016 1 1132114

(51) Int. Cl.
| | |
|---|---|
| *C07D 487/04* | (2006.01) |
| *A61K 31/5517* | (2006.01) |
| *A61P 25/20* | (2006.01) |
| *A61P 25/22* | (2006.01) |
| *A61P 25/08* | (2006.01) |
| *A61P 21/02* | (2006.01) |
| *A61P 23/00* | (2006.01) |
| *A61K 9/00* | (2006.01) |
| *A61K 9/08* | (2006.01) |
| *A61K 9/19* | (2006.01) |

(52) U.S. Cl.
CPC .......... *C07D 487/04* (2013.01); *A61K 9/0019* (2013.01); *A61K 9/08* (2013.01); *A61K 9/19* (2013.01); *A61K 31/5517* (2013.01); *A61P 21/02* (2018.01); *A61P 23/00* (2018.01); *A61P 25/08* (2018.01); *A61P 25/20* (2018.01); *A61P 25/22* (2018.01); *C07B 2200/13* (2013.01)

(58) Field of Classification Search
CPC ... C07D 487/04; A61K 31/5517; A61P 25/22; A61P 25/20; A61P 25/08; A61P 21/02; A61P 23/00
USPC .......................................... 540/505; 514/221
See application file for complete search history.

(56) References Cited

U.S. PATENT DOCUMENTS

| | | | |
|---|---|---|---|
| 2015/0148338 A1 | 5/2015 | Graham et al. | |
| 2015/0224114 A1* | 8/2015 | Kondo | A61K 45/06 514/171 |

FOREIGN PATENT DOCUMENTS

| | | |
|---|---|---|
| CN | 101501019 A | 8/2009 |
| CN | 103221414 A | 7/2013 |
| CN | 104768557 A | 7/2015 |
| CN | 104968348 A | 10/2015 |
| CN | 106380470 A | 2/2017 |
| WO | 2008/007051 A1 | 1/2008 |

OTHER PUBLICATIONS

International Search Report from International Application No. PCT/CN2016/109564, dated Aug. 3, 2017.
Written Opinion from International Application No. PCT/CN2016/109564, dated Aug. 3, 2017.

* cited by examiner

*Primary Examiner* — Venkataraman Balasubramanian
(74) *Attorney, Agent, or Firm* — Merchant & Gould P.C.

(57) ABSTRACT

The present invention provides a hydrobromide of methyl 3-[(4s)-8-bromo-1-methyl-6-(2-pyridyl)-4H-imidazol[1,2-a][1,4]benzodiazepine-4-yl] propionate and its related crystal forms, preparation method and use thereof. The hydrobromide has excellent solubility (>100 mg/ml), which is significantly superior to other currently commercially available or developed salt products, and is especially suitable for the preparation of injections, has relatively good stability in various crystal forms, and has good practical value and market prospects.

20 Claims, 10 Drawing Sheets

HYDROBROMIDE OF BENZODIAZEPINE DERIVATIVE, PREPARATION METHOD AND USE THEREOF

CROSS-REFERENCE TO RELATED APPLICATION

This application is a National Stage Application of PCT/CN2016/109564, filed Dec. 13, 2016, which claims benefit of CN201611132114.7 filed on Dec. 9, 2016, the disclosures of which applications are incorporated herein by reference. To the extent appropriate, a claim of priority is made to each of the above disclosed applications.

TECHNICAL FIELD

The present invention relates to hydrobromide of benzodiazepine derivative, preparation method and use thereof, and belongs to the field of medical chemistry.

BACKGROUND ART

Remimazolam, the chemical name of which is methyl 3-[(4s)-8-bromo-1-methyl-6-(2-pyridyl)-4H-imidazol[1,2-a][1,4]benzodiazepine-4-yl] propionate, has the structure represented by formula (I):

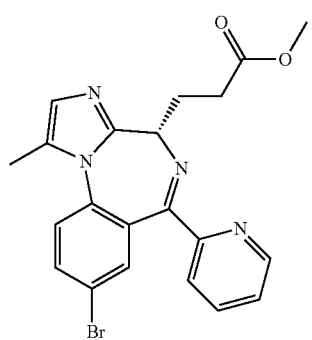

(I)

The compound is currently known to be a short-acting Central Nervous System (CNS) inhibitor with sedative, hypnotic, anxiolytic, muscle-relaxing and anticonvulsant effects. At present, it is mostly used for intravenous administration in the following clinical treatment regimens: for pre-operative sedation, anxiolytic and amnestic use during surgery; for conscious sedation during short-term diagnosis, surgery or endoscopic procedures; as a component for induction and maintenance of general anesthesia before and/or at the same time of administering other anesthetics and analgesia; for ICU sedation and the like. It is reported in the patent application CN101501019 that the free base of the compound has poor stability, and is only suitable for storage at a low temperature of 5° C., and, under the condition of 40° C./75% relative humidity (open), the sample is deliquescent, discolored, and significantly reduced in content.

In view of the stability problem with the free base of the compound, salts of the compound have been studied by researchers in multiple countries. For example, the patent applications CN101501019B and WO2008/007081 A1 respectively reported besylate and esylate of the compound of the formula (I). It is shown that the above salts have good thermal stability, low hygroscopicity and high water solubility. Moreover, CN104968348A clearly indicated that the above-mentioned besylate and esylate are the most preferred salts of the compound of the formula (I).

Immediately thereafter, CN103221414B proposed a tosylate of the compound of the formula (I), and indicated that the tosylate is less toxic than besylate, and some crystal forms thereof behave better in thermal stability, water solubility, etc.

By sorting the prior art information, the following related contents can be obtained (Table 1):

TABLE 1

| Name | Company | Patent No. | Properties |
| --- | --- | --- | --- |
| Remimazolam besylate (CNS-7056) | PAION | CN200780028964.5 CN201310166860.8 | Solubility in water: 8.3 mg/ml; degradation 0.5% at 40 degrees, RH75% closed, 4 weeks |
| Remimazolam tosylate (HR-7056) | Jiangsu Hengrui | CN201280003321.6 | Solubility in water: about 10, 11 mg/ml; influence factor tests show that the most stable crystal form still behaves not ideal under light conditions, with degradation more than 1.5% in 10 days. The patent states that the salt is less toxic than benzene sulfonic acid |
| Remimazolam esylate | Cambridge(GB) | US20100075955 | Solubility in water: 7.8 mg/ml; degradation 0.2% at 40 degrees, RH75% closed, 4 weeks |
| Remimazolam | GSK | WO 00/69836 | Almost insoluble in water; degradation 1.5-8%, and yellowing at 40 degrees, RH75% closed and 60 degrees open, 34 days |

It can be seen from the above table, neither the free base of remimazolam nor known salt derivatives of remimazolam has a water solubility higher than 11 mg/ml. The solubility is only in the range of sparingly soluble, which will increase its safety risk in clinical use, and require long-term vibration dissolution during clinical redissolution, and may also leave insoluble materials, resulting in inaccurate drug dosage and potential safety risks. In addition, when used for indications which require a large amount of drug, such as general anesthesia, the amount of diluent will be increased, resulting in extreme inconvenience in clinical use. Therefore, the solubility of known salt derivatives of remimazolam is a major disadvantage and needs to be further improved.

Contents of the Invention

In view of the existing water solubility problem with the free base of remimazolam and its related salts, the object of the present invention is to improve the solubility of remimazolam to a degree that is easily soluble in water (30-100 mg/ml). In order to achieve the above water solubility goal, the inventors have conducted studies from various aspects, e.g., crystal forms of existing salts, preparation excipients, formation of new salt types, etc., hoping to find a feasible means that can improve water solubility while ensuring better druggability. However, the screening study on crystal forms of existing salts, preparation excipients ended in failure and no more suitable method was found. In the study of various salt types, a total of more than 20 types of acid salts were involved in the screening of the preliminary test, and 8 salt types were found out, among which sulfate, 2-naphthalenesulfonate, mesylate, oxalate, hydrobromide, hydrochloride, 1,5-naphthalene disulfonate are crystalline, and ethanedisulfonate is amorphous. After further study on the above salts, the results are obtained as follows:

relatively low solubility, while mesylate has relatively low crystallinity, and is not easy to form a drug.

As can be seen from the above table, the solubility and other properties of hydrochloride and hydrobromide are relatively ideal. Among 1,356 chemically-defined organic drugs marketed before 2006 that are included in the US FDA Orange Book (Progress in Pharmaceutical Sciences, 2012, Vol. 36, No. 4,151), there are 523 (38.6%) drugs that are acid addition salts, of which the most frequently used acid to form salts with organic bases is hydrochloric acid (53.4%). It can be seen that, among the numerous acid addition salt-based drugs currently on the market, hydrochloride is preferred.

However, the analytic results of the stability of hydrochloride indicate that the most widely used hydrochloride has extremely poor stability:

TABLE 3

| | | Formulation Hydrochloride (moisture 8.58%) | |
|---|---|---|---|
| Item | purity | purity difference | appearance |
| 0 day | 96.84 | / | white-like solid |
| 5 days light-open | 96.37 | 0.47 | light yellow solid |
| light-closed | 94.69 | 2.15 | white-like solid |
| 60° C.-open | 94.01 | 2.83 | white-like solid |
| 60° C.-closed | 11.97 | 84.87 | black solid |
| 40° C.-open | 18.52 | 78.32 | brown solid |
| 40° C.-closed | 87.42 | 9.42 | light brown solid |
| 75% RH | 96.75 | 0.09 | white-like solid |
| 92.5% RH | 82.67 | 14.17 | light yellow solid (obvious moisture absorption) |

TABLE 2

| Compound | Crystal form | Crystallinity | Category | Salt forming ratio HPLC | IC | mp. (° C.) | Hygroscopicity (%) | Solubility in water (mg/mL) | Polymorphism |
|---|---|---|---|---|---|---|---|---|---|
| Free base | amorphous | amorphous | amorphous | NA | NA | NA | 1.7 | almost insoluble | NA |
| Sulfate | (bi)sulfate form 1 | relatively low | anhydrate | 1:1 | 1:1 | 124 | 0.1 | >100 | 2 |
| | (bi)sulfate form 2 | general | anhydrate | 1:2 | 1:1 | 186 | 24.9 | >100 | |
| Ethanedisulfonate | amorphous | amorphous | amorphous | decomposed | NA | NA | 26 | >100 | NA |
| Hydrochloride | hydrochloride form 1 | general | hydrate | NA | 1:1 | 194 | 2.8 | >100 | 2 |
| 1,5-naphthalene disulfonate | crystal form 1 | crystal form 1 | anhydrate | 1:1 | NA | | 15.9 | 1 | 1 |
| 2-naphthalenesulfonate | crystal form 1 | crystal form 1 | anhydrate | 1:1 | NA | 193 | 2.1 | 1 | 1 |
| Hydrobromide | crystal form α | crystal form α | anhydrate | NA | 1:1 | 170 | 2.5 | >100 | 4 |
| | crystal form 1 | crystal form 1 | hydrate | NA | 1:1 | 161 | 4.6 | >100 | |
| | crystal form 2 | crystal form 2 | hydrate | NA | 1:1 | 173 | | >100 | |
| | crystal form 3 | crystal form 3 | hydrate | NA | 1:1 | 163 | 5 | >100 | |
| Mesylate | Mesylate form 1 | relatively low | anhydrate | decomposed | NA | 165 | 24 | >100 | 1 |

Among them, sulfate, hydrobromide, hydrochloride have polymorphism. Sulfate has high hygroscopicity or relatively low crystallinity, and is not easy to form a drug. 1,5-Naphthalene disulfonate and 2-naphthalenesulfonate have It can be seen from Table 3 that, although hydrochloride has good water solubility, its stability is extremely poor, so hydrochloride is abandoned.

The present inventors unexpectedly found in the long-term study of the above various salts that hydrobromide of the compound of the formula (I) has excellent solubility (>100 mg/ml), is significantly superior to other currently marketed or developed salts of the compound, is especially suitable for the preparation of injections and also has relatively good stability in various crystal forms (see Table 3). For the above reasons, the present invention actually provides a hydrobromide of the compound of the formula I:

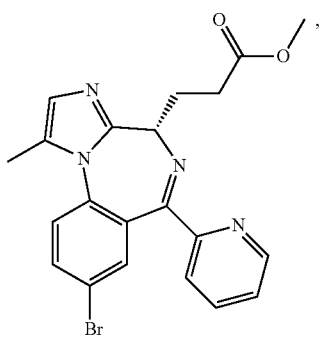

(I)

wherein, the stoichiometric ratio of the compound of the formula (I) to hydrobromic acid is 1:1.

The present inventors also found in the study that the hydrobromide of the compound of the formula (I) exists in various crystal forms, and, up to now, four crystal forms which are respectively named as I, II, III and α crystal forms have been found. The inventors studied and compared the physical and chemical properties of different crystal forms, and finally found that α crystal form has the best stability, and still retains good water solubility. Based on the above-mentioned good solubility, the crystal form can be prepared into a preparation (such as an injection) that has a relatively high requirement on the solubility of main drug, and in view of its good stability, the injection may not be limited to a powder for injection (powder-injection), but that a liquid injection (water-injection) can also be prepared.

The current study showed that the light degradation impurity of the compound of the formula (I) has the structure:

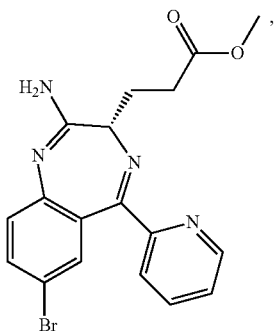 [SMILES: COC(=O)CC[C@@H]1N=C(c2ccccn2)c2cc(Br)ccc2N=C1N]

while the degradation impurity under other conditions is mainly

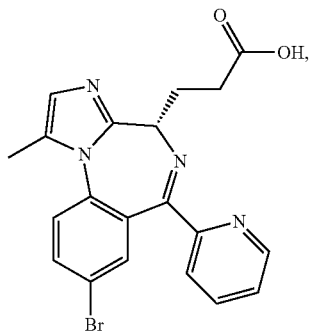 [SMILES: Cc1cnc2n1-c1ccc(Br)cc1C(c1ccccn1)=N[C@H]2CCC(=O)O]

the impurity having an activity which is 1/300 of that of the compound of formula (I). If the above compound or salt derivative thereof is inferior in stability, and is liable to be degraded, it may cause a reduction in pharmacological activity, and may even cause a certain toxic side effect to human body. Whether the stability is good or not is also a key factor in selecting the crystal form of the compound. Accordingly, it is preferred in the present invention that the hydrobromide of the compound of the formula (I) is present in the form of α crystal form. By comparing the X-ray powder diffraction pattern (Cu-ka radiation) of the α crystal form with those of other three crystal forms, it is found that the α crystal form has distinct characteristic peaks at angle 2θ of about 13.7±0.2, 16.0±0.2, 19.2±0.2 degrees. In the differential scanning calorimetry of the α crystal form, there is a melting endothermic peak at 170° C.±2° C. Therefore, in the present invention, the structure of the α crystal form is defined by the above-mentioned powder diffraction characteristic peaks and DSC melting peak, and on the basis of this definition, the α crystal form can be clearly distinguished from other three crystal forms.

Of course, in addition to the above three distinct distinguishing characteristic peaks, the X-ray powder diffraction pattern of the α crystal form includes characteristic peaks at angle 2θ of about 8.2±0.2, 10.3±0.2, 12.6±0.2, 15.1±0.2, 20.7±0.2, 22.8±0.2, 23.2±0.2, 25.5±0.2, 26.2±0.2, 27.7±0.2, 28.4±0.2, 30.7±0.2 degrees.

The X-ray powder diffraction pattern of the α crystal form prepared in the specific embodiments of the present invention is as shown in FIG. 3 or 4, and the DSC spectrum is as shown in FIG. 5.

According to the EMEA document [20080124 EMEA A letter on the assessment of genotoxic impurities], it is pointed out that there is a potential risk with lower sulfonic acids such as benzene sulfonic acid and toluene sulfonic acid, that is, if an alcohol is used in the process, it may lead to the production of genotoxic impurity—besylate or tosylate, and likewise, the use of an alcohol-cleaned reaction tank or storage tank may also increase this risk. Therefore, in addition to the above-mentioned advantages of water solubility and stability, hydrobromide may also have a great advantage in terms of safety, because hydrobromic acid has low toxicity, and bromide ion is one of the 16 trace elements in human body.

The present invention also provides a preparation method of the α crystal form of the hydrobromide as described above, which comprises the following steps:

(1) reacting a compound of the formula I with hydrobromic acid in a solvent system consisting of isopropanol and water to obtain crystal form III, preferably with an aqueous solution of hydrobromic acid in isopropanol to precipitate out crystal form III, or crystallizing hydrobromide in isopropanol solvent to obtain crystal form III;

(2) exposing the crystal form III to a gas having a high relative humidity at a certain temperature until the crystal form III is transformed into α crystal form.

Wherein, in the step (2), the temperature is between 50 and 60° C.

Wherein, in the step (2), the high relative humidity means a relative humidity of 65% or more.

Further, the high relative humidity means a relative humidity of 75% or more.

In a specific embodiment of the present invention, the gas is air.

The above-mentioned transformation method may also be referred to as gas phase-mediated transformation, which is different from solvent-mediated transformation, and the medium for gas phase-mediated transformation is a gas. The transformation time can be from several hours to several days, weeks or months, depending on the relative humidity and temperature, which can be determined by conventional analysis means.

Based on their excellent solubility (>100 mg/ml), the hydrobromide of the compound of the formula (I) and its various crystal forms can be used to prepare injections, which can better meet the requirements of injections for the solubility of raw materials. Accordingly, the present invention also provides use of the hydrobromide for the preparation of an injection having a sedative or hypnotic effect.

The sedative or hypnotic effect mentioned in the present invention is directed to mammals. At the same time, the drug also has certain effects of anti-anxiety, inducing muscle relaxation, anticonvulsant, and anesthesia. For the specific administration dose, reference may be made to the effective dose of remimazolam in the prior art.

Further, the present invention provides a pharmaceutical composition comprising a hydrobromide as described above. Of course, in addition to hydrobromide, pharmaceutically acceptable excipients may also be included in the composition.

"Pharmaceutically acceptable" as used in the present invention is meant to include any substance that does not interfere with the effectiveness of biological activity of active ingredient and is non-toxic to the host to which it is administered.

"Excipient" is a general term for all additional materials other than main drug in a pharmaceutical preparation. Excipient should have the following properties: (1) non-toxic to human body, with almost no side effects; (2) chemically stable, not susceptible to temperature, pH, preservation time, etc.; (3) not incompatible with the main drug, not affecting the efficacy and quality inspection of the main drug; (4) incapable of interacting with the packaging material.

In a specific embodiment of the invention, the pharmaceutical composition is in the form of a preparation for injection.

Among them, the injection is selected from the group consisting of a liquid injection (water-injection), a sterile powder for injection (powder-injection) or a tablet for injection (i.e., a molded tablet or a machine tablet made from a drug by sterile operation method, which, when used, is dissolved in water for injection, for subcutaneous or intramuscular injection).

Among them, the powder for injection contains at least an excipient in addition to the hydrobromide of the compound of the formula (I). The excipient in the present invention is an ingredient intentionally added to a drug, which should not have pharmacological properties in the amount used, but the excipient may contribute to the processing, solubility or dissolution of drugs, the delivery of drugs by targeted route of administration, or contribute to the stability.

The excipient of the present invention may be selected from the group consisting of carbohydrates, inorganic salts, and polymers, or a combination of two or more thereof. Among them, the carbohydrate includes monosaccharides, oligosaccharides or polysaccharides.

Monosaccharide is a sugar that cannot be further hydrolyzed. It is a basic unit of making up molecules of various disaccharides and polysaccharides. It can be divided into triose, tetrose, pentose, hexose, etc. Monosaccharides in nature are mainly pentose and hexose. For example, glucose is aldohexose and fructose is ketohexose.

Oligosaccharide, also known as oligose, is a polymer resulted from condensation of a few (2-10) monosaccharides.

Polysaccharide is a polymeric high molecular carbohydrate composed of sugar chains bound by glycosidic bonds and resulted from more than 10 monosaccharides.

The mass ratio of the compound of the formula (I) to the excipient is (1:0.5)(1:200). In view of cost, concentration of active ingredient, etc., it is proposed in the present invention that the mass ratio of the compound of the formula (I) to the excipient be 1:5 to 1:86.

The sterile powder for injection in the present invention can be obtained by a conventional process such as aseptic dispensing or freeze drying.

In a specific embodiment of the present invention, the carbohydrate-based excipient is selected from the group consisting of lactose, maltose, sucrose, mannitol, and glucose, or a combination of two or more thereof. In a specific embodiment of the present invention, the inorganic salt is selected from the group consisting of sodium chloride, potassium chloride, calcium chloride and the like. Of course, at present, in lyophilized powder for injection, inorganic salts are often used in combination with carbohydrates. Therefore, in actual operation, the type of excipient in the present invention can be conventionally selected according to known theory. For example, it is possible to use lactose, mannitol or glucose alone or a combination of two or more thereof, or to further add an inorganic salt such as sodium chloride on the basis of using one or more carbohydrates.

In the course of study, the present inventors found that, when a lyophilized powder for injection is prepared using the hydrobromide of the compound of the formula (I) as raw material, a plurality of different excipients can be selected to achieve good stability and resolubility, and the lyophilized powder for injection is superior to remimazolam besylate lyophilized powder for injection (CN201380036582.2). This finding is sufficient to demonstrate that the remimazolam hydrobromide provided by the present invention is more suitable for the preparation of lyophilized powder for injections.

It is apparent that, on the basis of the above contents of the present invention, various other forms of modifications, substitutions or changes may be made in accordance with the common technical knowledge and means in the art, without departing from the basic technical idea of the present invention.

The above contents of the present invention will be further described in detail below by way of specific embodiments. However, the scope of the above-mentioned subject matter of the present invention should not be construed as being limited to the following embodiments. Any technique

SPECIFIC MODE FOR CARRYING OUT THE INVENTION

The raw material, the compound of the formula (I) (remimazolam), used in the present invention can be commercially obtained, or can be prepared according to a known method (e.g., patents US200, 700, 934, 75A, etc.).

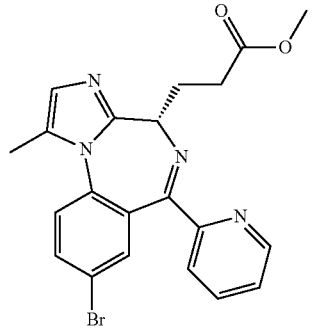

(I)

Example 1 Preparation of Crystal Form III of the Hydrobromide of the Compound of the Formula (I)

Figure 1:
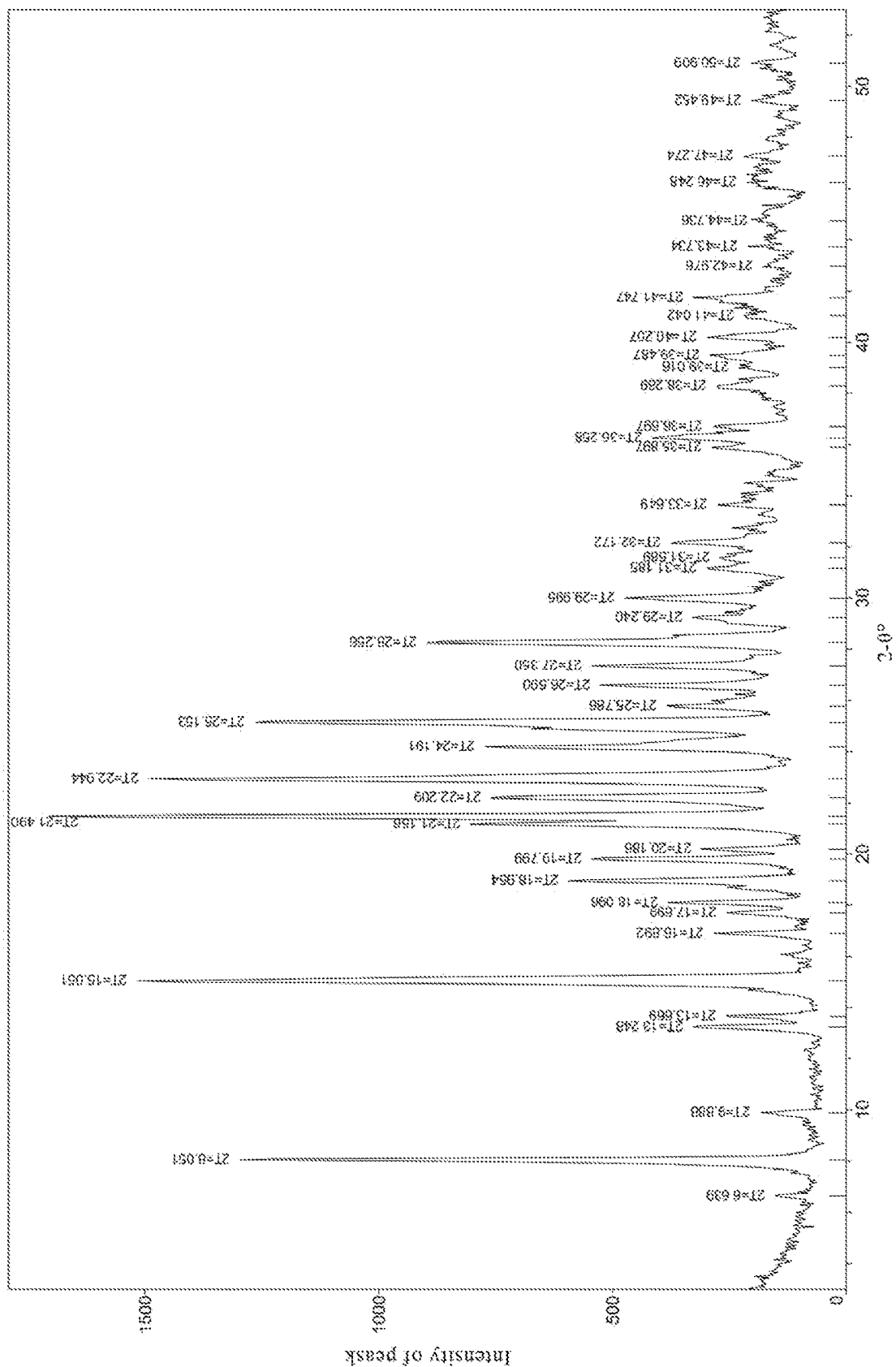
FIG. 1 is an X-ray powder diffraction pattern of crystal form III of the hydrobromide of the compound of the formula (I)
Figure 2:
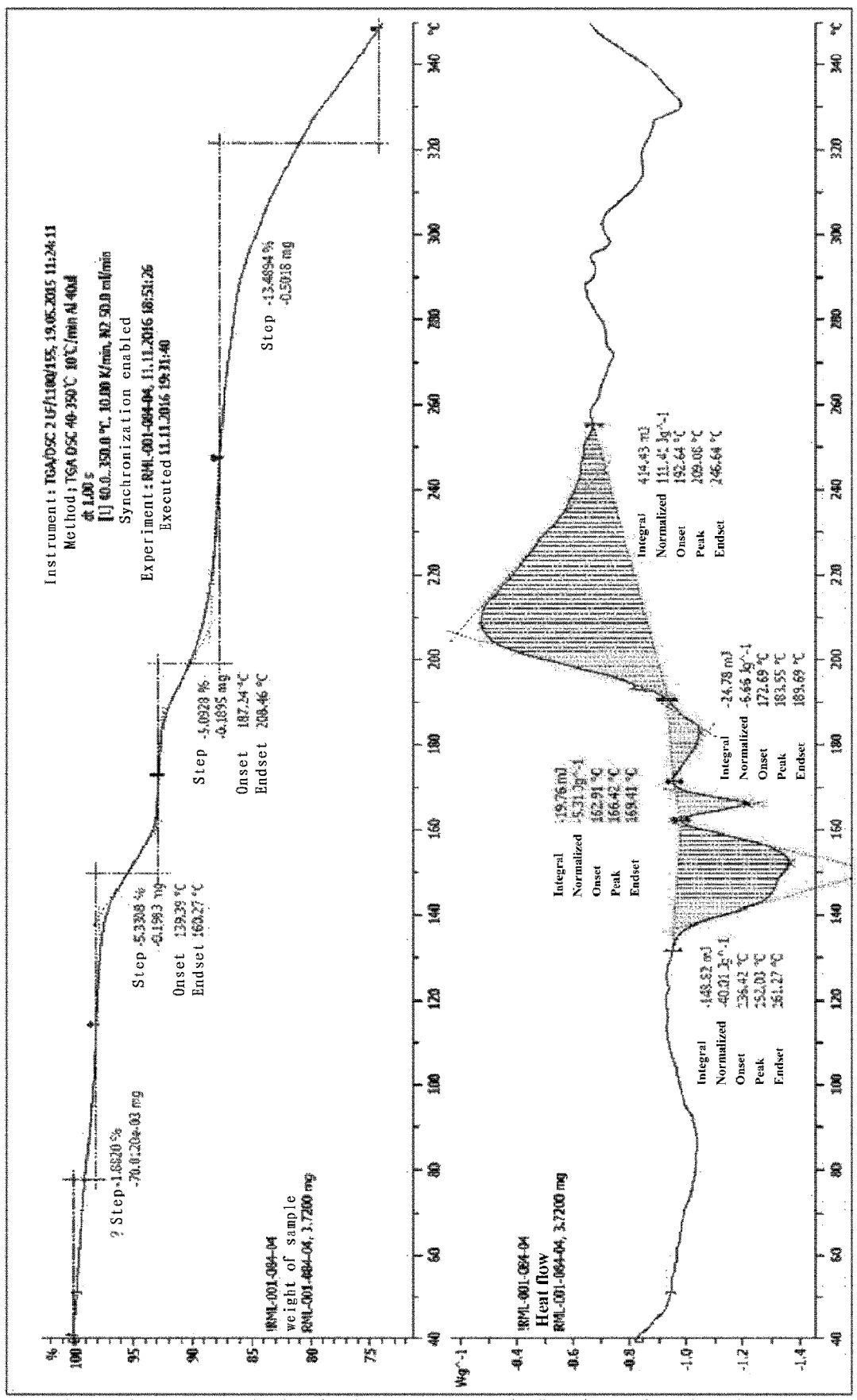
FIG. 2 is a DSC spectrum of crystal form III of the hydrobromide of the compound of the formula (I)

1.8 g of the compound of the formula (I) was accurately weighed into a 100 mL three-necked flask, 8.2 mL of isopropanol was added and stirred till complete dissolution; 0.83 g of an 47% aqueous solution of hydrobromic acid was dissolved in 6.3 mL of isopropanol, and added dropwise to the solution of the compound of the formula (I) in isopropanol; the resulting mixture was stirred and crystallized, filtered, and dried under reduced pressure at 55° C. to obtain a hydrobromide of the compound of the formula (I). The X-ray diffraction pattern of the crystal was shown in FIG. 1, the DSC and TGA spectra were shown in FIG. 2, and the melting point is 163° C. This crystal form was defined as crystal form III of the hydrobromide of the compound of the formula (I).

Example 2: Preparation of α Crystal Form of the Hydrobromide of the Compound of the Formula (I)

The crystal form III of the hydrobromide could be transformed in a non-flowing gas with a certain humidity, especially in the air with a humidity of 75% or more, which was mediated through gas phase interface, to obtain α crystal form. The method had the advantages: not solvent mediated, no loss, and no solvent residue.

Figure 3:
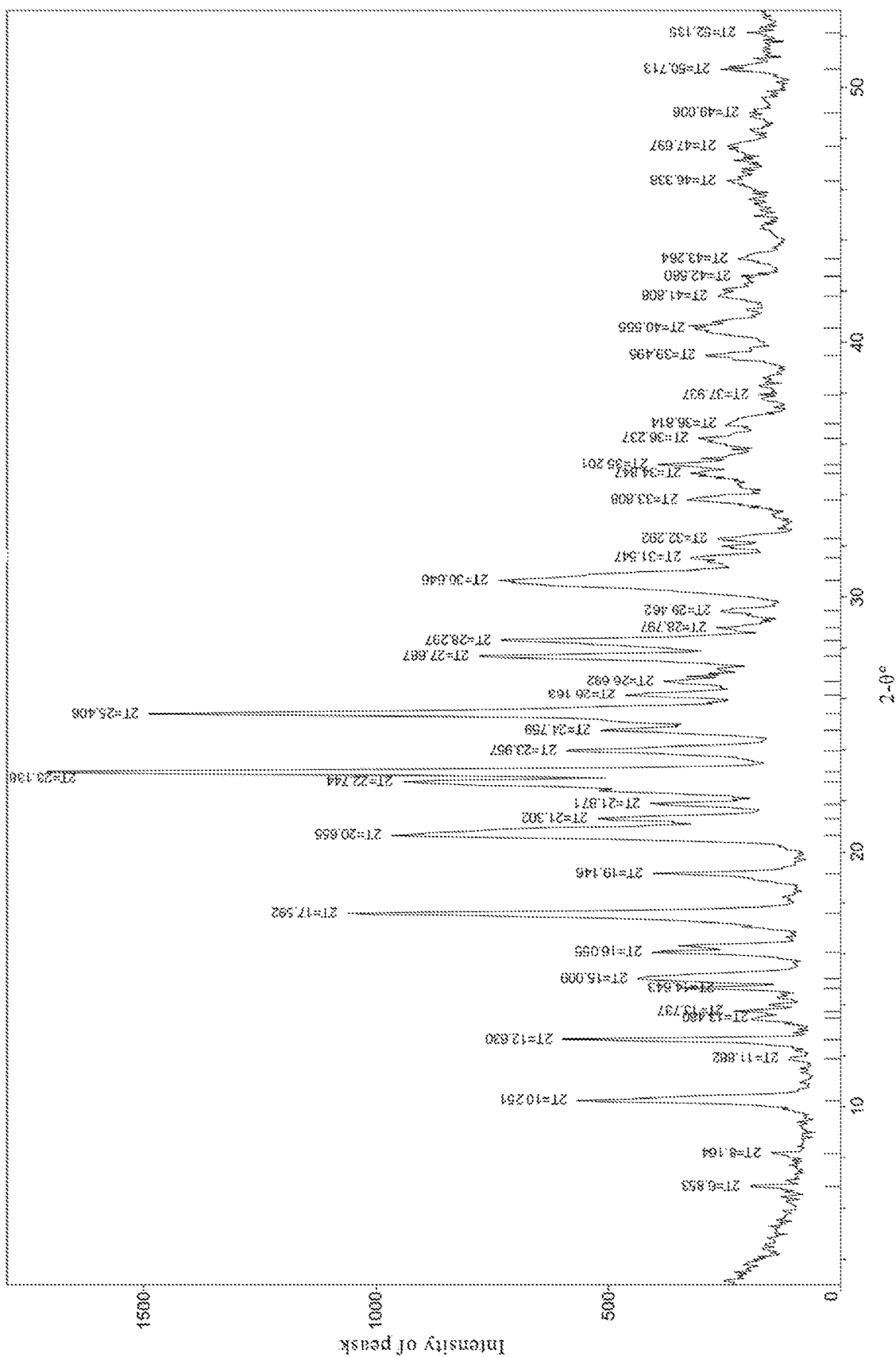
FIG. 3 is an X-ray powder diffraction pattern of α crystal form of the hydrobromide of the compound of the formula (I)

Specifically, 200 mg of the crystal form III of the hydrobromide of the compound of the formula (I) obtained above in Example 1 was placed open under the conditions of 50~55° C.-RH 75% for 20 hours. The X-ray diffraction pattern of the crystal sample was shown in FIG. 3, at about 6.85, 8.16, 10.25, 12.63, 13.48, 13.73, 15.01, 16.05, 16.25, 17.59, 19.15, 20.65, 22.74, 23.18, 23.95, 24.75, 25.40, 26.16, 27.69, 28.30, 30.65. The product was identified as α crystal form of the hydrobromide of the compound of the formula (I). IC: the bromide ion content was 15.74%, and the salt forming ratio of hydrobromic acid was confirmed to be 1:1; solvent residue: isopropanol 0.01%.

Example 3: Preparation of α Crystal Form of the Hydrobromide of the Compound of the Formula (I)

500 mg of the crystal form III of the hydrobromide of the compound of the formula (I) obtained above in Example 1 was placed open under the conditions of 55~60° C.-RH 75% for 60 hours. The X-ray diffraction pattern and the DSC spectrum of the crystal sample were studied and compared. The product was determined to be α crystal form of the hydrobromide of the compound of the formula (I).

Figure 4:
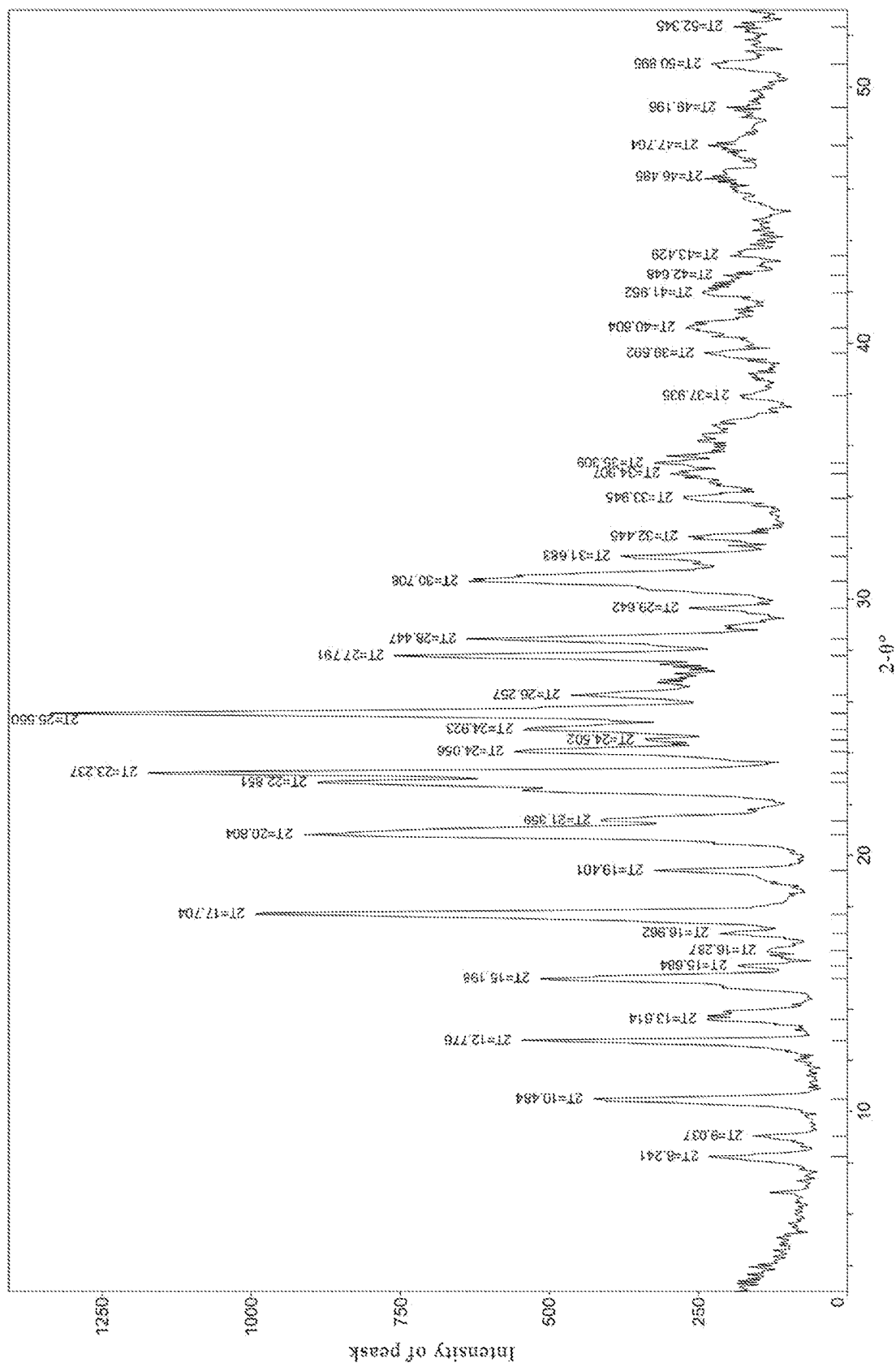
FIG. 4 is an X-ray powder diffraction pattern of α crystal form of the hydrobromide of the compound of the formula (I)
Figure 5:
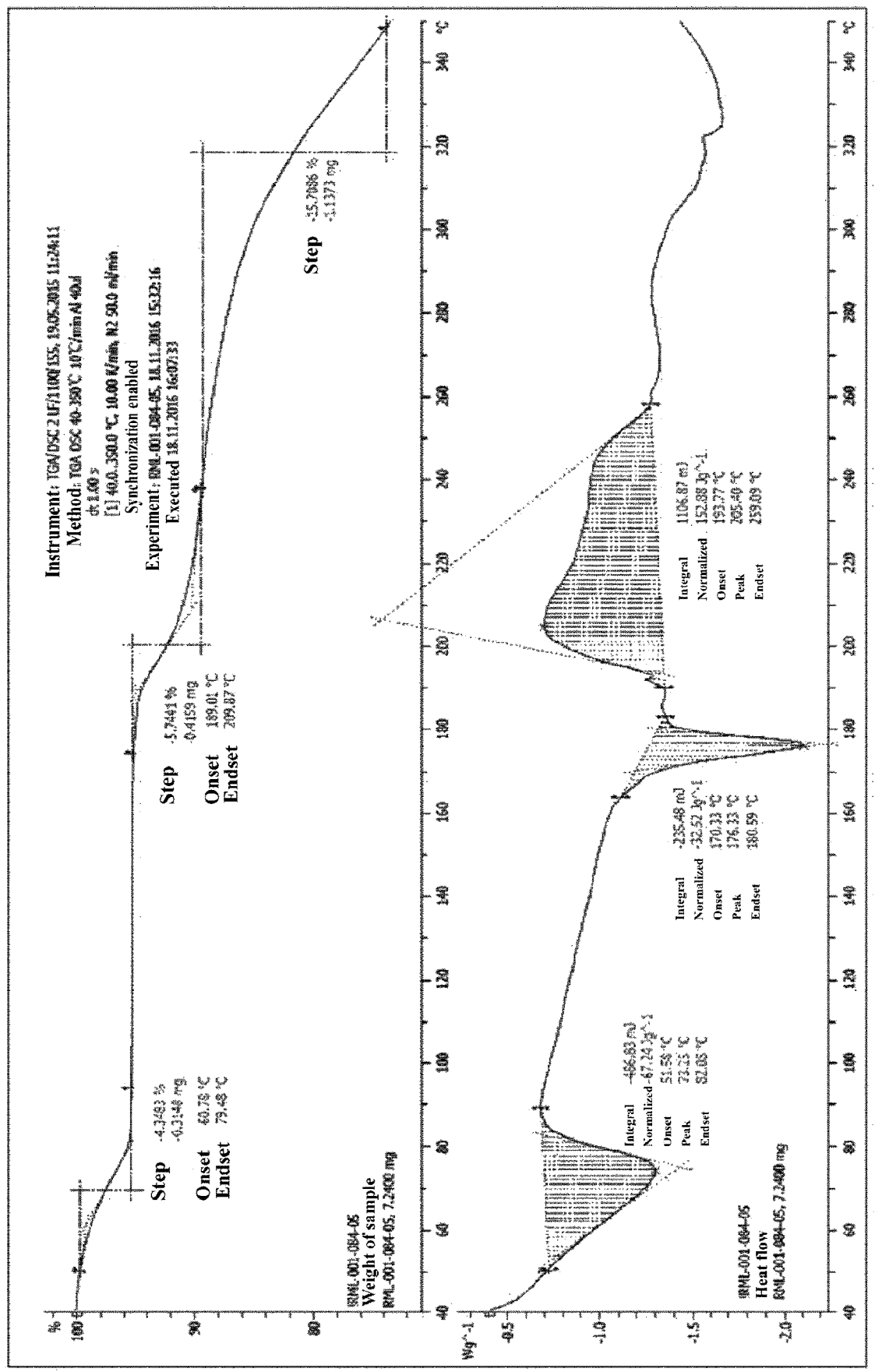
FIG. 5 is a DSC/TGA spectrum of α crystal form of the hydrobromide of the compound of the formula (I)
Figure 6:
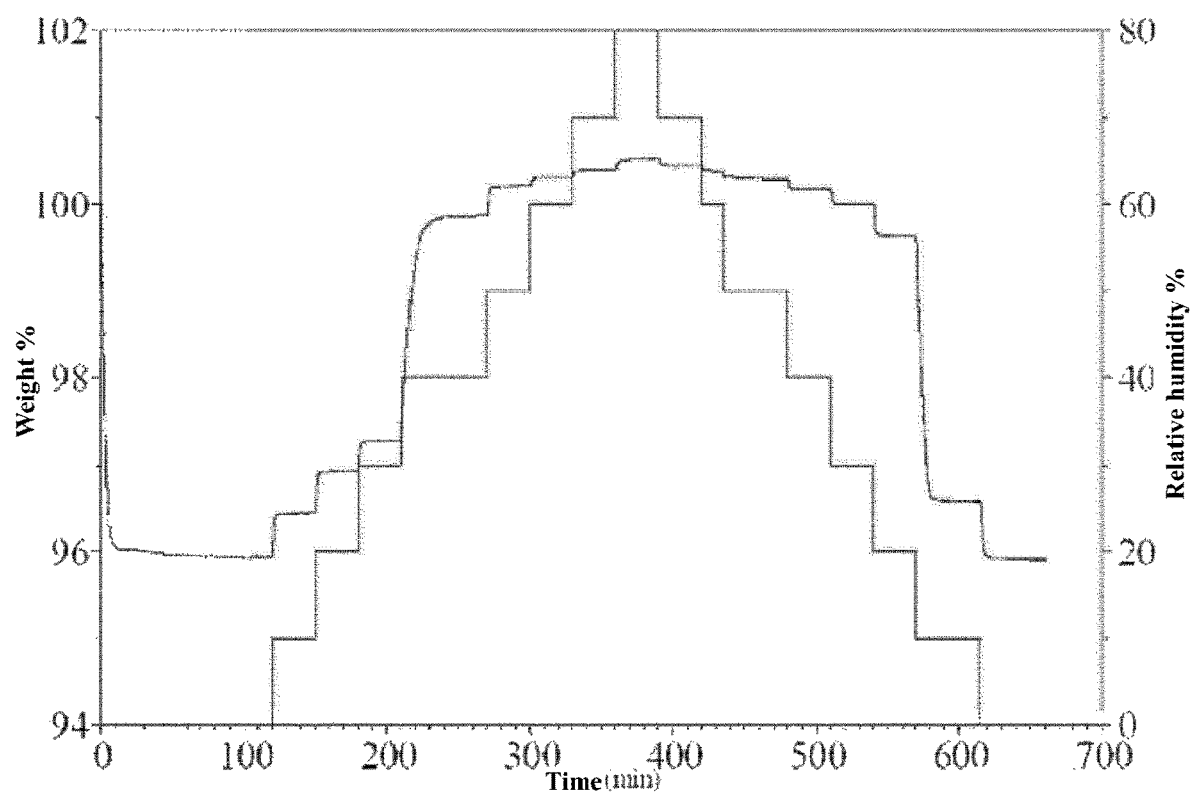
FIG. 6 is a DVS spectrum of α crystal form of the hydrobromide of the compound of the formula (I)

The X-ray diffraction pattern was shown in FIG. 4, at about 6.96, 8.24, 10.48, 12.77, 13.61, 13.85, 15.20, 16.05, 16.28, 17.70, 19.40, 20.80, 22.85, 23.23, 24.05, 24.92, 25.55, 26.25, 27.79, 28.45, 30.70; the DSC/TGA spectrum was shown in FIG. 5, showing a melting point 170° C.; as the sample was not further dried after transformation at 75% humidity, it contained 4.3% free water, which was embodied by a weight loss platform of 60.78-79.45° C. in TGA; in addition, the DVS spectrum showed the ability to combine with water at a certain humidity, and the product was α crystal form without crystal water. The product was determined to be α crystal form of the hydrobromide of the compound of the formula (I).

Example 4: Preparation of Crystal Form I of the Hydrobromide of the Compound of the Formula (I)

Figure 7:
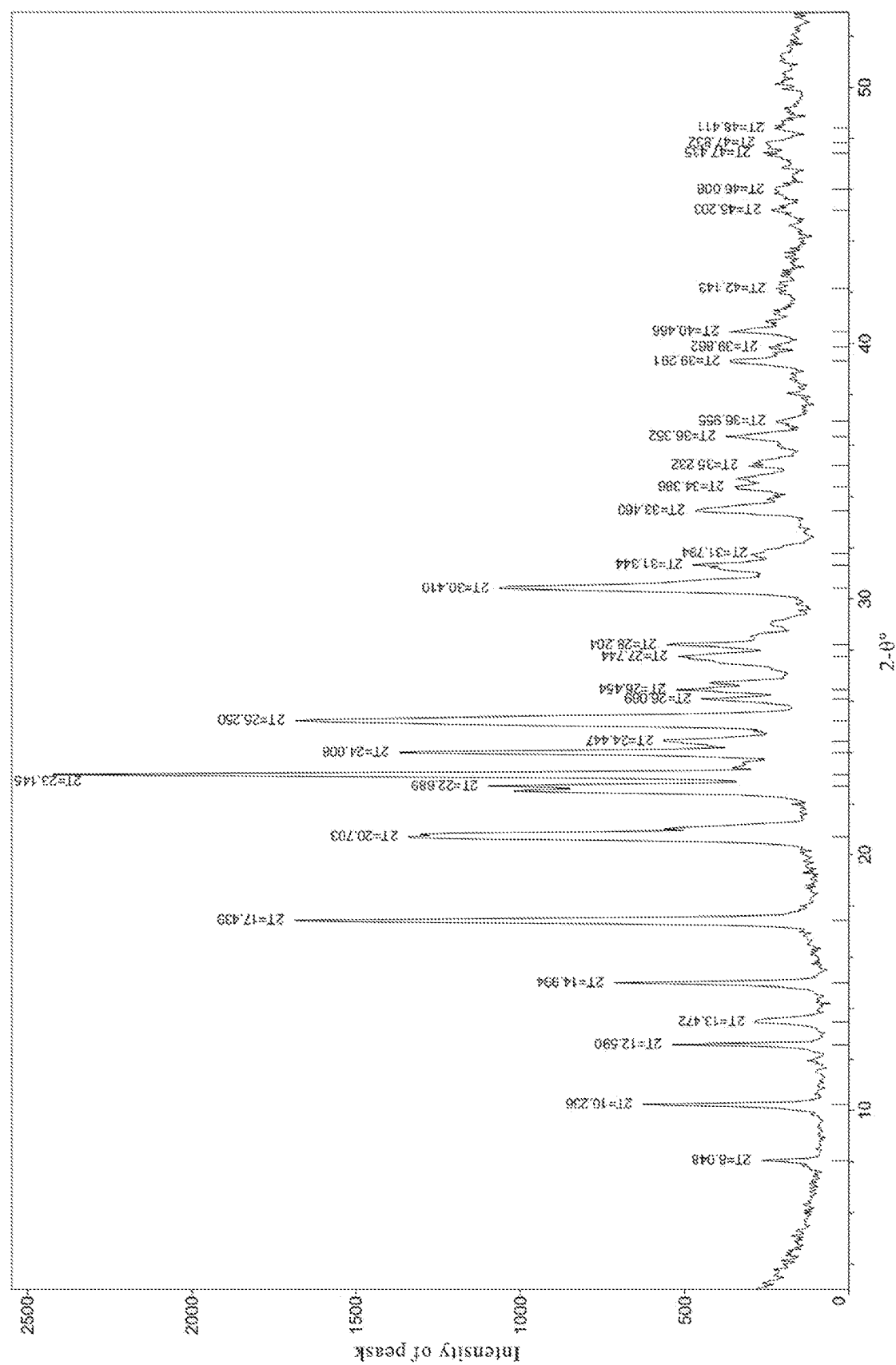
FIG. 7 is an X-ray powder diffraction pattern of crystal form I of the hydrobromide of the compound of the formula (I)
Figure 8:
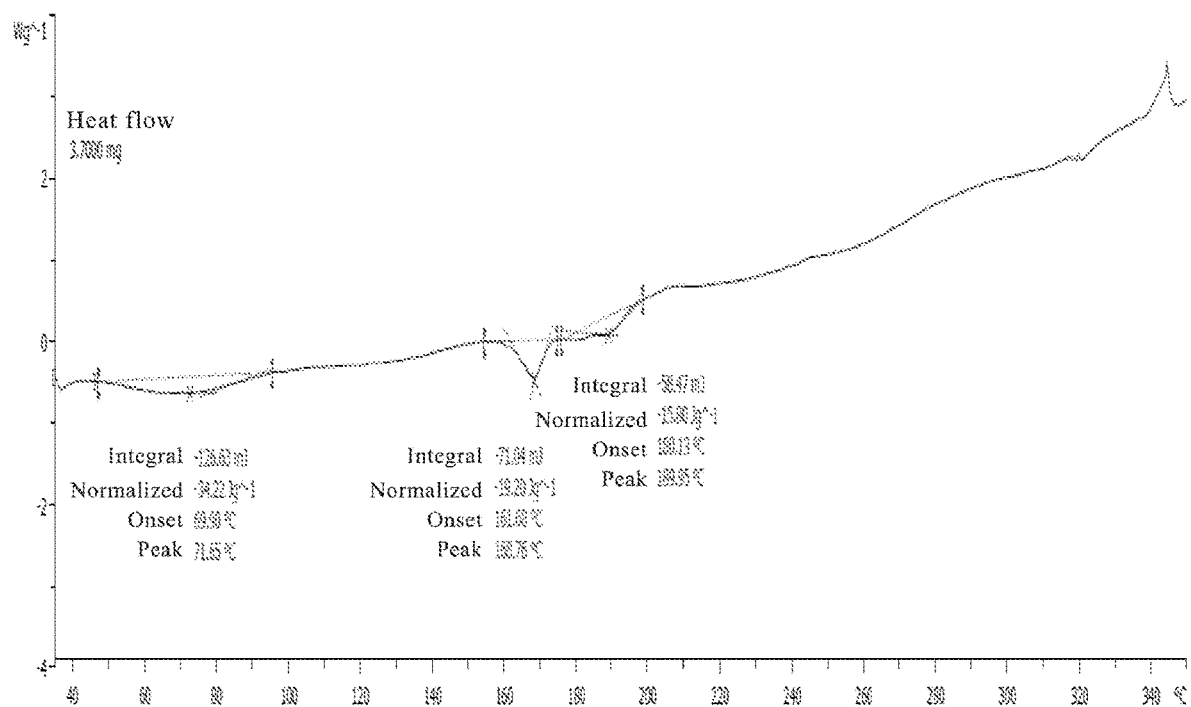
FIG. 8 is a DSC spectrum of crystal form I of the hydrobromide of the compound of the formula (I)
Figure 9:
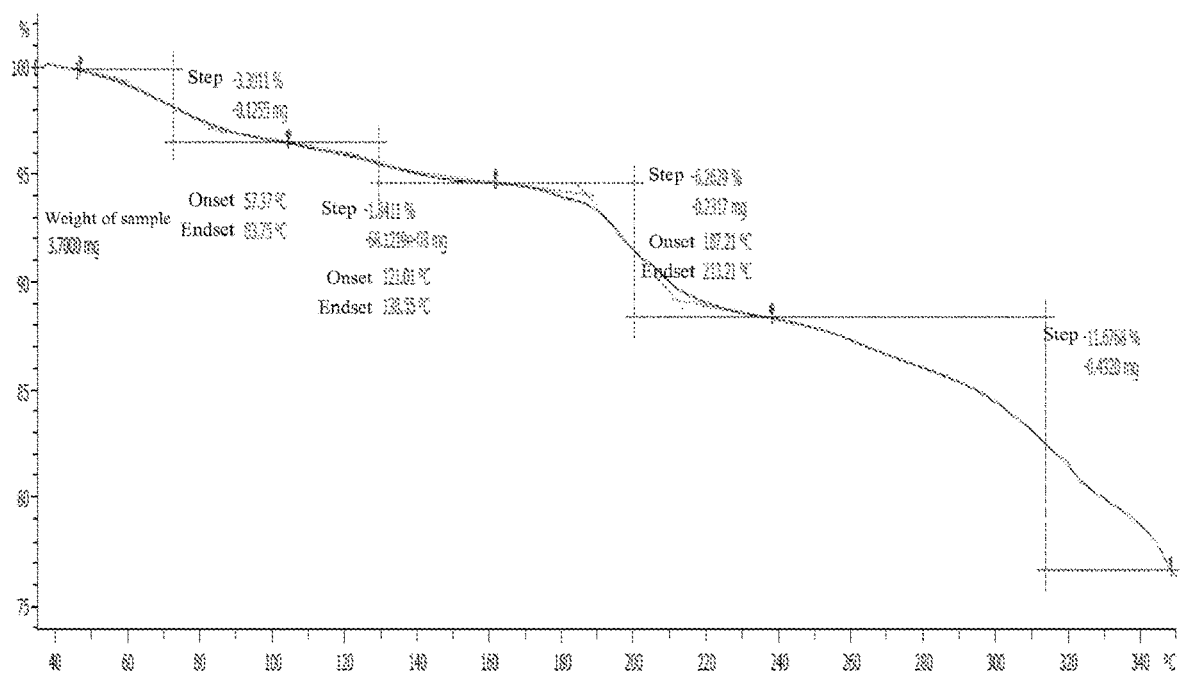
FIG. 9 is a TGA spectrum of crystal form I of the hydrobromide of the compound of the formula (I)

44 mg (0.10 mmol) of the compound of the formula (I) was accurately weighed into a 10 mL single-necked flask, 0.4 mL of ethyl acetate was added and stirred till complete dissolution, the reaction temperature was lowered to 4° C., and then 1.1 mL of a solution of hydrobromic acid in methanol (1 mol/L, 0.11 mmol) was added dropwise to the solution of the compound of the formula (I) in ethyl acetate, stirred and crystallized, suction filtered, rinsed with ethyl acetate, and dried under reduced pressure at 30° C. to obtain a hydrobromide of the compound of the formula (I), white solid 42 mg, yield 81%. The X-ray diffraction pattern of the crystal was shown in FIG. 7, and the DSC spectrum was shown in FIG. 8, having characteristic absorption peaks at around 70° C., 162° C. and 180° C. This crystal form was defined as crystal form I of the hydrobromide of the compound of the formula (I). The TGA spectrum of the crystal form I of the hydrobromide of the compound of the formula (I) was shown in FIG. 9.

Example 5: Preparation of Crystal Form II of the Hydrobromide of the Compound of the Formula (I)

22.26 mg of the compound of formula (I) was accurately weighed into a 1 mL centrifuge tube, 1004 of acetone was added and stirred till complete dissolution, then 10 mg of a 47% aqueous solution of hydrobromic acid was dissolved in 754 of acetone and added dropwise to the solution of the compound of the formula (I) in acetone, stirred and crystallized, centrifuged, and dried under reduced pressure at 30° C. to obtain a hydrobromide of the compound of the formula (I), white solid 20 mg, yield 76%.

Figure 10:
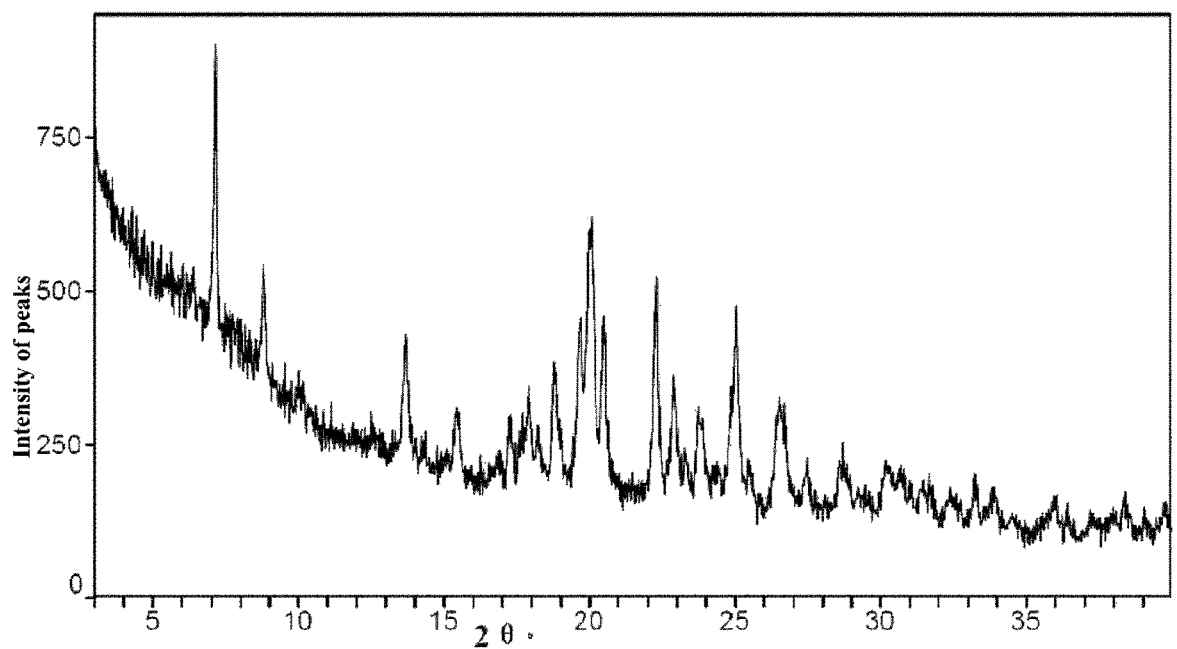
FIG. 10 is an X-ray powder diffraction pattern of crystal form II of the hydrobromide of the compound of the formula (I)
Figure 11:
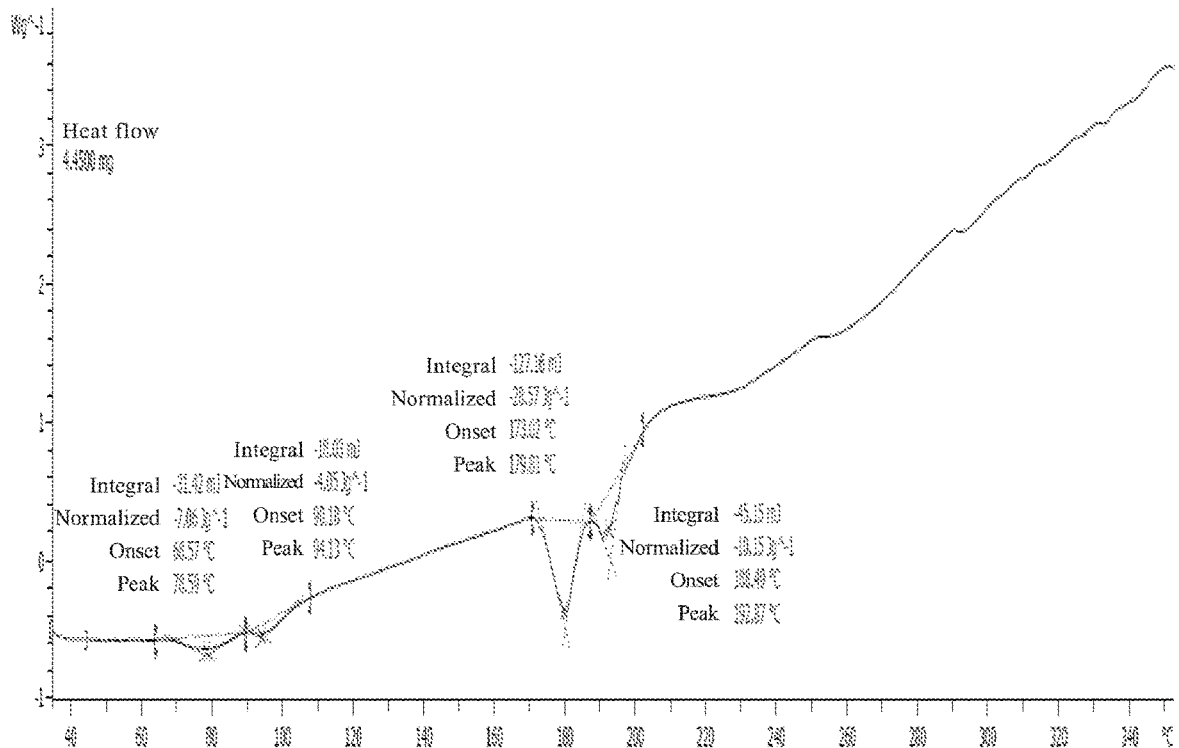
FIG. 11 is a DSC spectrum of crystal form II of the hydrobromide of the compound of the formula (I)
Figure 12:
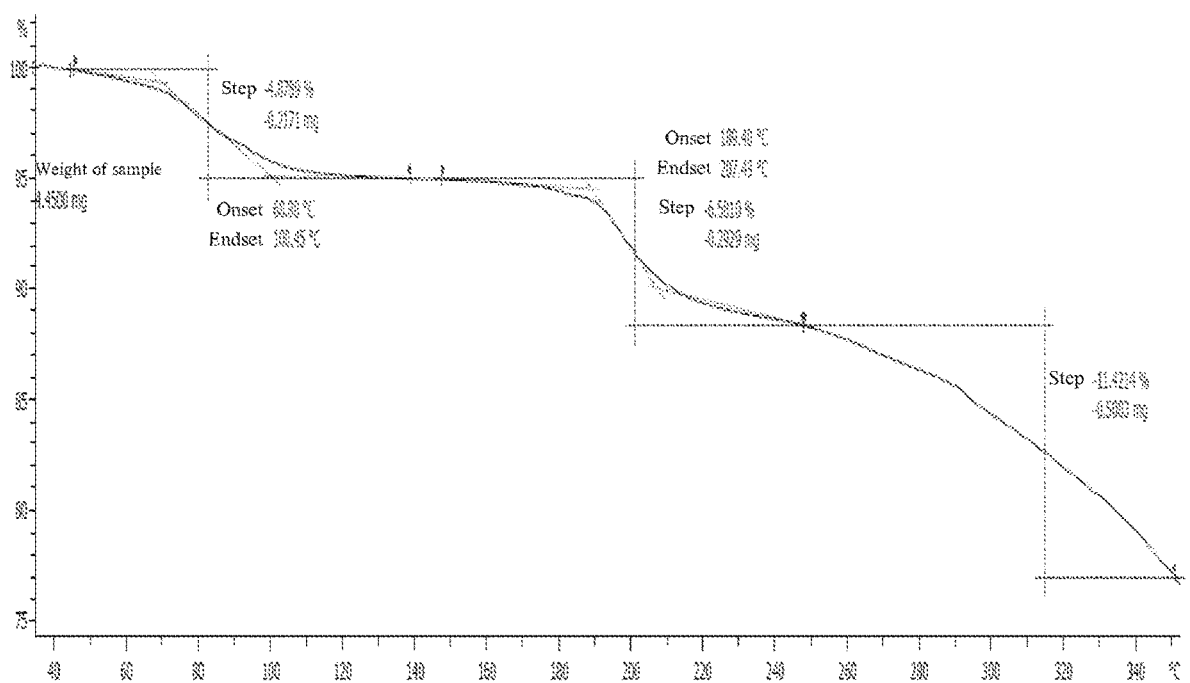
FIG. 12 is a TGA spectrum of crystal form II of the hydrobromide of the compound of the formula (I).

The X-ray diffraction spectrum of the crystal was shown in FIG. 10, and the DSC spectrum was shown in FIG. 11, having characteristic absorption peaks at around 69° C., 90° C., 173° C. and 188° C. This crystal form was defined as crystal form II of the hydrobromide of the compound of the formula (I). The TGA spectrum of the crystal form II of the hydrobromide of the compound of the formula (I) was shown in FIG. 12.

Example 6 Comparison Between α Crystal Form and Other Crystal Forms of the Present Invention The α crystal form of the hydrobromide of the compound of the formula (I) was compared with other crystal forms, the results shown in Table 4:

As can be seen from the above table, the α crystal form prepared in the present invention still could retain good stability under the conditions of strong light, high heat and high humidity, and was apparently superior to the other three crystal forms.

Example 7 Comparison in Stability Between the α Crystal Form of the Present Invention and the Original Innovative Crystal Form Crystal form I of besylate of the compound of the formula (I) was prepared according to the patents CN200780028964.5 and CN201310166860.8, and the obtained crystal form had characteristic peaks at about 7.19, 7.79, 9.38, 12.08, 14.06, 14.40, 14.72, 15.59.

The stability of the crystal form of the original innovative besylate was compared with that of the α crystal form of the hydrobromide of the present invention, the results shown in Table 5:

TABLE 5

| | Item | Hydrobromide (α crystal form) purity | Hydrobromide (α crystal form) purity difference | Besylate (crystal form I) purity | Besylate (crystal form I) purity difference |
|---|---|---|---|---|---|
| | 0 day | 99.76 | / | 99.24 | / |
| 10 days | light-open | 99.55 | −0.21 | 98.8 | −0.44 |
| | light-closed | 99.78 | 0.02 | 99.18 | −0.06 |
| | 60° C.-open | 99.72 | −0.04 | 99.18 | −0.06 |
| | 60° C.-closed | 99.78 | 0.02 | 99.07 | −0.17 |
| | 40° C.-open | 99.77 | 0.01 | 99.21 | −0.03 |
| | 40° C.-closed | 99.78 | 0.02 | 99.23 | −0.01 |
| | 75% RH | 99.77 | 0.01 | 99.23 | −0.01 |
| | 92.5% RH | 99.77 | 0.01 | 99.23 | −0.01 |
| 30 days | light-open | 99.26 | −0.5 | 98.09 | −1.15 |
| | light-closed | 99.78 | 0.02 | 99.16 | −0.08 |
| | 60° C.-open | 99.7 | −0.06 | 99.14 | −0.1 |

TABLE 4

| | Item | RML-007-056-1-zj α crystal form purity | RML-007-056-1-zj α crystal form purity difference | RML-007-056-1 crystal form 3 purity | RML-007-056-1 crystal form 3 purity difference | RML-007-049-1 crystal form 2 purity | RML-007-049-1 crystal form 2 purity difference | RML-002-066-1 crystal form 1 purity | RML-002-066-1 crystal form 1 purity difference |
|---|---|---|---|---|---|---|---|---|---|
| | 0 day | 99.76 | / | 99.79 | / | 99.87 | / | 99.48 | / |
| 10 days | light-open | 99.55 | −0.21 | 92.5 | −7.29 | 98.41 | −1.46 | 94.17 | −5.31 |
| | light-closed | 99.78 | 0.02 | 99.78 | −0.01 | 99.81 | −0.06 | 99.48 | 0 |
| | 60° C.-open | 99.72 | −0.04 | 99.59 | −0.2 | 99.64 | −0.23 | 99.45 | −0.03 |
| | 60° C.-closed | 99.78 | 0.02 | 99.66 | −0.13 | 99.84 | −0.03 | 99.46 | −0.02 |
| | 40° C.-open | 99.77 | 0.01 | 99.71 | −0.08 | 99.06 | −0.81 | 99.49 | 0.01 |
| | 40° C.-closed | 99.78 | 0.02 | 99.75 | −0.04 | 99.6 | −0.27 | 99.48 | 0 |
| | 75% RH | 99.77 | 0.01 | 99.78 | −0.01 | 99.82 | −0.05 | 99.5 | 0.02 |
| | 92.5% RH | 99.77 | 0.01 | 99.76 | −0.03 | 98.92 | −0.95 | 99.48 | 0 |
| 30 days | light-open | 99.26 | −0.5 | 93.4 | −6.39 | 98.14 | −1.73 | 82.17 | −17.31 |
| | light-closed | 99.78 | 0.02 | 99.76 | −0.03 | 99.83 | −0.04 | 99.35 | −0.13 |
| | 60° C.-open | 99.7 | −0.06 | 99.55 | −0.24 | 99.57 | −0.3 | 99.13 | −0.35 |
| | 60° C.-closed | 99.74 | −0.02 | 99.56 | −0.23 | 99.8 | −0.07 | 99.32 | −0.16 |
| | 40° C.-open | 99.74 | −0.02 | 99.67 | −0.12 | 97.47 | −2.4 | 99.15 | −0.33 |
| | 40° C.-closed | 99.75 | −0.01 | 99.74 | −0.05 | 99.02 | −0.85 | 99.33 | −0.15 |
| | 75% RH | 99.79 | 0.03 | 99.78 | −0.01 | 99.83 | −0.04 | 99.38 | −0.1 |
| | 92.5% RH | 99.76 | 0 | 99.73 | −0.06 | 99.47 | −0.4 | 99.31 | −0.17 |

TABLE 5-continued

| | Name: | | | |
|---|---|---|---|---|
| | Hydrobromide (α crystal form) | | Besylate (crystal form I) | |
| Item | purity | purity difference | purity | purity difference |
| 60° C.-closed | 99.74 | −0.02 | 99.15 | −0.09 |
| 40° C.-open | 99.74 | −0.02 | 99.12 | −0.12 |
| 40° C.-closed | 99.75 | −0.01 | 99.13 | −0.11 |
| 75% RH | 99.79 | 0.03 | 99.15 | −0.09 |
| 92.5% RH | 99.76 | 0 | 99.14 | −0.1 |

As can be seen from the above table, the α crystal form prepared in the present invention exhibited better stability than the crystal form of the original innovative besylate under the conditions of strong light, high heat and high humidity. In addition, it can be seen from the published data that the stability of the α crystal form prepared in the present invention was also better than that of the crystal form of tosylate in CN103221414B.

Example 8 Formulation and Preparation Process of Remimazolam Hydrobromide Sterile Powder for Injection According to the formulation of Table 6, a sterile powder was prepared according to the following preparation process, and the physical and chemical parameters of various formulations were compared.

Preparation Process:

Formulation 1: remimazolam hydrobromide was directly dispensed into a brown vial under aseptic conditions, and covered.

Formulations 2~10: Excipient and remimazolam hydrobromide were dissolved in water for injection, stirred until dissolution, the pH value of the solution was adjusted with hydrochloric acid/sodium hydroxide, and then the solution was dispensed into a vial, and lyophilized.

TABLE 6

Remimazolam hydrobromide sterile powder for injection

| | Formulation | | | | | | | | | |
|---|---|---|---|---|---|---|---|---|---|---|
| | Formulation 1 | Formulation 2 | Formulation 3 | Formulation 4 | Formulation 5 | Formulation 6 | Formulation 7 | Formulation 8 | Formulation 9 | Formulation 10 |
| Material | dose mg | dose g | dose g | dose g | dose g | dose g | dose g | dose g | dose g | dose g |
| remimazolam hydrobromide | 29 | 5.9 | 29.6 | 11.8 | 9.0 | 1.8 | 1.8 | 1.8 | 25.7 | / |
| remimazolam besylate | / | / | / | / | / | / | / | / | / | 29.5 |
| Lactose | / | 1.5 | / | 50 | 250 | / | 130 | / | 375 | 375 |
| Mannitol | / | 1.0 | 125 | / | / | 85 | / | 170 | / | / |
| Glucose | / | / | / | 50 | / | / | / | 170 | / | / |
| Sodium chloride | / | / | / | / | / | 5 | / | / | / | / |
| Hydrochloric acid/sodium hydroxide to adjust the pH | / | 3.15 | 3.18 | 3.13 | 3.20 | 3.08 | 3.17 | 3.25 | 3.11 | 3.10 |
| Water for Injection | / | to 1000 ml | to 1000 ml | to 100 ml | to 1000 ml | to 1000 ml | to 1000 ml | to 1000 ml | to 1000 ml | to 1000 ml |

The physical and chemical parameters of various formulations were given as follows:

TABLE 7

Physical and chemical parameters of remimazolam hydrobromide sterile powder for injection

| Physical and chemical properties | Formulation 1 | Formulation 2 | Formulation 3 | Formulation 4 | Formulation 5 | Formulation 6 | Formulation 7 | Formulation 8 | Formulation 9 | Formulation 10 |
|---|---|---|---|---|---|---|---|---|---|---|
| Description | white solid | white solid | white solid | white solid | white solid | white solid | white solid | white solid | white solid | white solid |
| Moisture | ≤3% | ≤3% | ≤3% | ≤3% | ≤3% | ≤3% | ≤3% | ≤3% | ≤3% | ≤3% |
| Redissolution time | within 30 s | within 30 s | within 30 s | within 30 s | within 30 s | within 30 s | within 30 s | within 30 s | within 30 s | 240 s |
| Appearance | powdery | good | good | good | good | good | good | Slight collapse | good | good |

Formulations 9, 10 were remimazolam hydrobromide lyophilized powder for injection, remimazolam besylate lyophilized powder for injection that were respectively prepared according to the process reported in the patent CN201380036582.2, and comparison was made between them as follows:

TABLE 8

Comparison between remimazolam hydrobromide lyophilized powder for injection and original innovative remimazolam besylate lyophilized powder for injection

| Name Item | Remimazolam hydrobromide lyophilized powder for injection (Formulation 9) | | | | Remimazolam besylate lyophilized powder for injection (Formulation 10) | | | |
|---|---|---|---|---|---|---|---|---|
| | description | purity | purity difference | redissolution time | Description | purity | purity difference | redissolution time |
| 0 day | white solid | 99.84 | / | within 30 s | white solid | 99.74 | / | 240 s |
| Accelerated 1 month | white solid | 99.78 | −0.06 | within 30 s | white solid | 99.54 | −0.20 | 240 s |
| Accelerated 2 months | white solid | 99.73 | −0.11 | within 30 s | white solid | 99.32 | −0.42 | 240 s |
| Accelerated 3 months | white solid | 99.67 | −0.17 | within 30 s | white solid | 99.48 | −0.26 | 240 s |
| Accelerated 6 months | white solid | 99.53 | −0.31 | within 30 s | white solid | 98.78 | −0.96 | 240 s |
| Long-term 3 months | white solid | 99.82 | −0.02 | within 30 s | white solid | 99.63 | −0.11 | 240 s |
| Long-term 6 months | white solid | 99.75 | −0.09 | within 30 s | white solid | 99.53 | −0.21 | 240 s |

Notes:
1. Accelerated placement condition was 40° C.; Long-term placement condition was 25° C.
2. Redissolution time: gently vibrating with water for injection/glucose/normal saline till complete dissolution and uniform mixture, and recording the time required for complete dissolution.

As can be seen from the above table, the remimazolam hydrobromide lyophilized powder for injection of the present invention retained good stability in both accelerated stability test and long-term stability test, and it was superior in both stability and resolubility to the remimazolam besylate lyophilized powder for injection (CN201380036582.2).

The invention claimed is:

1. A hydrobromide of the compound of the formula I:

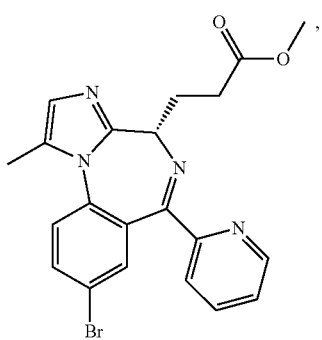

(I)

wherein the stoichiometric ratio of the compound of the formula (I) to hydrobromic acid is 1:1.

2. The hydrobromide as claimed in claim 1, wherein the hydrobromide is present in the form of α crystal form, and the X-ray powder diffraction pattern obtained using Cu-kα radiation at least includes characteristic peaks at angle 2θ of about 13.7±0.2, 16.0±0.2, 19.2±0.2 degrees.

3. The hydrobromide as claimed in claim 2, wherein the X-ray powder diffraction pattern of the α crystal form of the hydrobromide further includes characteristic peaks at angle 2θ of about 8.2±0.2, 10.3±0.2, 12.6±0.2, 15.1±0.2, 20.7±0.2, 22.8±0.2, 23.2±0.2, 25.5±0.2, 26.2±0.2, 27.7±0.2, 28.4±0.2, 30.7±0.2 degrees.

4. The hydrobromide as claimed in claim 2, wherein the differential scanning calorimetry of the α crystal form, there is a melting endothermic peak at 170° C.±2° C.

5. A preparation method of the α crystal form of the hydrobromide as claimed in claim 3, which comprises the following steps:
(1) reacting a compound of the formula I with hydrobromic acid in a solvent system consisting of isopropanol and water to obtain crystal form III of a hydrobromide;
(2) exposing the crystal form III to a gas having a high relative humidity at a certain temperature until the crystal form III is transformed into α crystal form.

6. The preparation method as claimed in claim 5, wherein step (1) is carried out by reacting with an aqueous solution of hydrobromic acid in isopropanol to precipitate out crystal form III, or crystallizing hydrobromide in isopropanol solvent to obtain crystal form III.

7. The preparation method as claimed in claim 5, wherein the temperature of step (2) is between 50 and 60° C.

8. The preparation method as claimed in claim 5, wherein the high relative humidity means a relative humidity of 65% or more in step (2).

9. The preparation method as claimed in claim 8, wherein the high relative humidity means a relative humidity of 75% or more.

10. The preparation method as claimed in claim 5, wherein the gas of step (2) is air.

11. A method for producing the effect of sedation, hypnosis, anti-anxiety, inducing muscle relaxation, anticonvulsant or anesthesia in a subject, comprising administrating the subject an injection of the hydrobromide as claimed in claim 3.

12. A pharmaceutical composition, wherein the composition is a preparation for injection comprising the hydrobromide as claimed in claim 3.

13. The pharmaceutical composition as claimed in claim 12, wherein the preparation for injection is selected from the group consisting of a liquid injection, and a sterile powder for injection.

14. The pharmaceutical composition as claimed in claim 13, wherein the sterile powder for injection contains at least an excipient in addition to the hydrobromide of the compound of the formula (I).

15. The pharmaceutical composition as claimed in claim 14, wherein the excipient is selected from the group consisting of carbohydrates, inorganic salts, and polymers, or a combination of two or more thereof.

16. The pharmaceutical composition as claimed in claim 15, wherein the carbohydrate is selected from the group consisting of monosaccharides, oligosaccharides or polysaccharides.

17. The pharmaceutical composition as claimed in claim 16, wherein the carbohydrate is selected from the group consisting of lactose, maltose, sucrose, mannitol, glucose, and glucan.

18. The pharmaceutical composition as claimed in claim 15, wherein the inorganic salt is selected from the group consisting of sodium chloride, potassium chloride, and calcium chloride.

19. The pharmaceutical composition as claimed in claim 14, wherein the mass ratio of the compound of the formula (I) to the excipient is 1:0.5~1:200.

20. The pharmaceutical composition as claimed in claim 19, wherein the mass ratio of the compound of the formula (I) to the excipient is 1:5 to 1:86.

* * * * *